(12) United States Patent
Haneckow et al.

(10) Patent No.: US 11,903,871 B2
(45) Date of Patent: Feb. 20, 2024

(54) SIPHON APPARATUS

(71) Applicants: Benjamin Haneckow, Kalamazoo, MI (US); Lindsey Haneckow, Kalamazoo, MI (US); Sunshine Gail Wooden, Lawton, MI (US)

(72) Inventors: Benjamin Haneckow, Kalamazoo, MI (US); Lindsey Haneckow, Kalamazoo, MI (US); Sunshine Gail Wooden, Lawton, MI (US)

( * ) Notice: Subject to any disclaimer, the term of this patent is extended or adjusted under 35 U.S.C. 154(b) by 18 days.

(21) Appl. No.: 17/300,498

(22) Filed: Jul. 20, 2021

(65) Prior Publication Data

US 2022/0087857 A1 Mar. 24, 2022

Related U.S. Application Data

(60) Provisional application No. 63/103,141, filed on Jul. 20, 2020.

(51) Int. Cl.
*A61F 7/00* (2006.01)
*A63F 9/00* (2006.01)

(52) U.S. Cl.
CPC .............. *A61F 7/0085* (2013.01); *A63F 9/00* (2013.01); *A61F 2007/0002* (2013.01); *A63F 2250/0421* (2013.01)

(58) Field of Classification Search
CPC ............ A61F 7/0085; A61F 2007/0002; A63F 9/00; A63F 2250/0421
USPC ........................................................ 239/72
See application file for complete search history.

(56) References Cited

U.S. PATENT DOCUMENTS

| | | | | |
|---|---|---|---|---|
| 245,839 A * | 8/1881 | Karcheski | ............... | F04F 10/00 137/212 |
| 308,070 A * | 11/1884 | Hartmann | ............ | A47G 19/183 215/4 |
| 451,862 A * | 5/1891 | Moncrieff | ............ | B67D 1/0425 222/394 |
| 654,597 A * | 7/1900 | Brady | ...................... | A01J 11/12 137/145 |
| 959,779 A * | 5/1910 | Mills | ........................ | A01J 11/12 137/145 |
| 1,036,640 A * | 8/1912 | Kendal | ..................... | A01J 11/12 137/145 |
| 1,042,365 A * | 10/1912 | Meyer | ..................... | E03D 1/085 4/373 |
| 1,876,860 A * | 9/1932 | Cooney | .................. | G01F 11/084 215/3 |
| 2,055,334 A * | 9/1936 | Bukoski | .................. | G01F 11/28 222/416 |

\* cited by examiner

*Primary Examiner* — Justin M Jonaitis (57) ABSTRACT

Invention is related to water used in combination with outdoor activity; which can include, recreation activities, therapeutic activities, exercise activities. Outdoor activity can be utilized by a user, or more than one user. Recreation activities can provide multiple user interface in a game format. Therapeutic activity can include, a smoking cessation modality, an improved immune system modality, a virus fighting modality which may include covid or related. Exercise activities can include, calorie burning, flexibility, strength, breathwork. Method can use a siphon water delivery. Invention can be used as a lawn watering device. Method can be supported with an app or other related technology, social media interface.

1 Claim, 12 Drawing Sheets

SIPHON APPARATUS

BACKGROUND

Field of Invention

An outside water game can be used for entertainment purposes. Lawn watering device can apply water to a surface can relate to outdoor exercise, meditation, physical therapy, can relate to new use for a bucket bottle or other.

Description of Prior Art

Prior art problems. U.S. Pat. No. 4,813,680 is a game with liquid release worn upon head. Any user who doesn't want water spilled on head would not be interested. U.S. Pat. No. 5,992,853 Game where a player is sprayed with water if answered question wrong any user who doesn't want to answer questions would not be interested. U.S. Pat. No. 5,154,671 a water slide with pool and spray arch. Mostly appeals to younger users and provides a chance for injury. U.S. Pat. No. 10,342,695 a cold mist sprayer is only designed for limited point of contact of cold. U.S. Pat. No. 9,556,187 a method for cold therapy with heat exchanger is space wasteful and has many components to break. U.S. Pat. No. 11,058,223 a fitness tracking software to motivate users is limited to users who want conventional exercise. U.S. Pat. No. 11,067,424 a bucket accessory doesn't offer any therapeutic effects.

SUMMARY

In accordance with present application present invention provides an intermittent delivery of a liquid with a siphon to produce any found usefulness. Invention also provides for intermittent pauses between cold doses. Invention can be used as a time to exercise, to stretch, to practice a yoga breathing, a yoga asana, to play a game.

REFERENCE NUMERALS IN DRAWINGS

| | |
|---|---|
| 10 Water Supply | 70 siphon inlet |
| 10c Water Supply | 80 siphon check valve |
| 10h Water Supply | 100 siphon centerline |
| 20 bucket high level | 110 siphon weir |
| 30 bucket | 120 siphon apex |
| 32 bucket vent | 130 siphon dip |
| 34 bucket lid | 140 dip top |
| 36 bucket assembly | 142 dip apex |
| 40 Siphon | 150 dip bottom |
| 42 cooperative siphon supply | 160 siphon outlet |
| 44a siphon | 160a siphon outlet |
| 44b siphon | 160b siphon outlet |
| 44c siphon | 160c siphon outlet |
| 170 delivery device | |
| 180 user | |
| 180 user | |
| 180b user | |
| 180c user | |
| 190 appurtenance | |
| 190 appurtenance | |
| 120a siphon apex | |
| 120b siphon apex | |
| 120c syphon apex | |
| 120d siphon apex | |
| 200 Usefulness | |

DESCRIPTION OF METHOD

Figure 1:
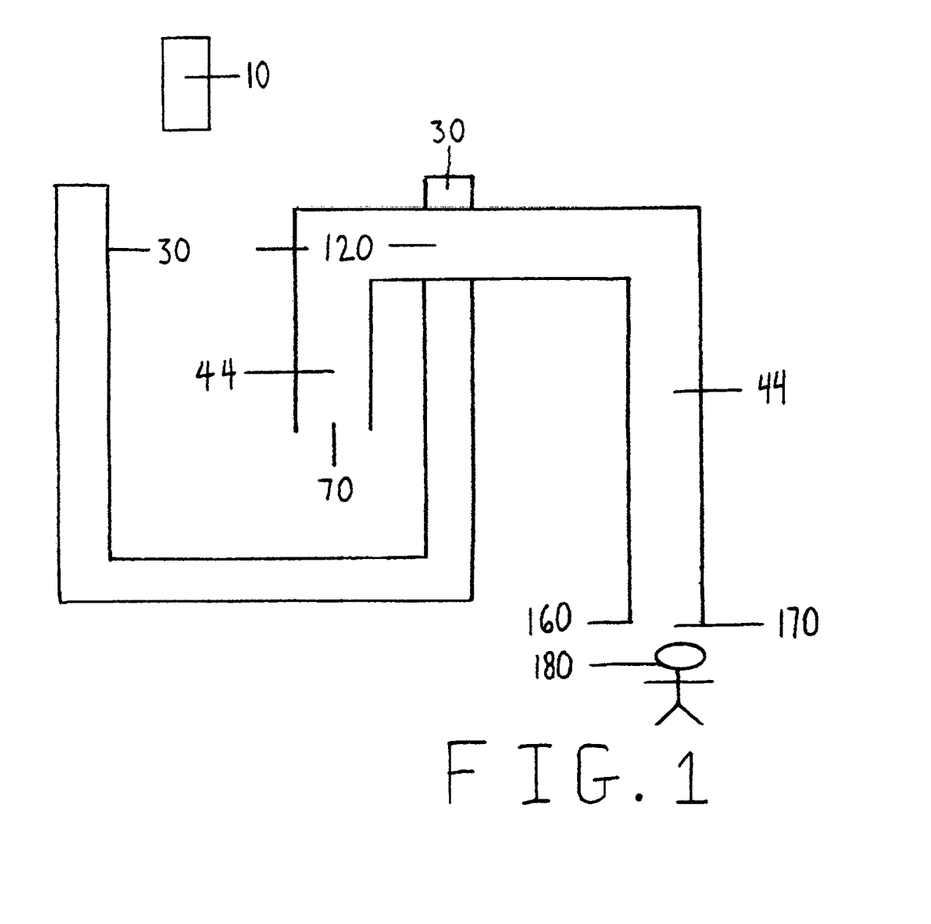
FIG. 1 shows a side view of example of method a siphonic assembly 44

FIG. 1 shows a basic version of method including any water supply 10 which can be sourced from stored rain water, city water pipes, a well, or any other source of water. Water supply can have a contributing feature of temperature, or quality of temperature. Water supply 10 can be cold water cool water warm water or hot water, any temperature that make method useful.

A bucket 30 can be a bucket or any device able to hold water, to contain water, to process water in a anyway useful. Bucket 30 can be modified in any way to make method useful. Modifications can be to have holes placed to allow components of method to make method useful. Bucket 30 can be modified in way to make water tight connections with components of method, can be modified to allow to drain with components of method.

A siphon 44 can be any device capable of transferring a liquid particularly in the form of a siphon, having the ability to move a liquid from a height to a lower height but first to a higher height. Siphon 44 can be a pipe, a tube.

FIG. 1 shows a version of method including any water supply 10 which can be sourced from rain water. Water supply 10 can have contributing feature of temperature, or quality of temperature. Water supply 10 can be cold water cool water warm water or hot water, any temperature that make method useful.

A bucket 30 can be a bucket or any device able to hold water, to contain water to process water.

Bucket 30 can be a bottle. Bucket 30 can be modified in way to make method useful. Bucket 30 can be modified in any way to make water tight connections with components of method, can be modified in any way to allow water to drain when not in use.

A siphon 44 can be any device capable of transferring a liquid particularly in the form of a siphon, having the ability to move a liquid from a height to a lower height after moving to a higher height, Siphon 44 can be a pipe, a tube, a device of any shape profile, can be built integral into bucket 30.

A delivery device 170 can be any device that can work in conjunction with water supply 10 as it exits siphon 44 at siphon outlet 160.

Delivery device 170 can have a flow control property device such as a valve or any other adjustable flow device.

Delivery Device 170 can be any device which work in conjunction with water supply 10 as it exit siphon 44 at siphon outlet 160 at a location in conjunction with person 180.

Delivery device 170 can be in any location, delivery device 170 can be located away from siphon outlet 160 but still affect water supply 10 as it exit siphon 44 at siphon outlet 160 location in conjunction with person 180.

Figure 2:
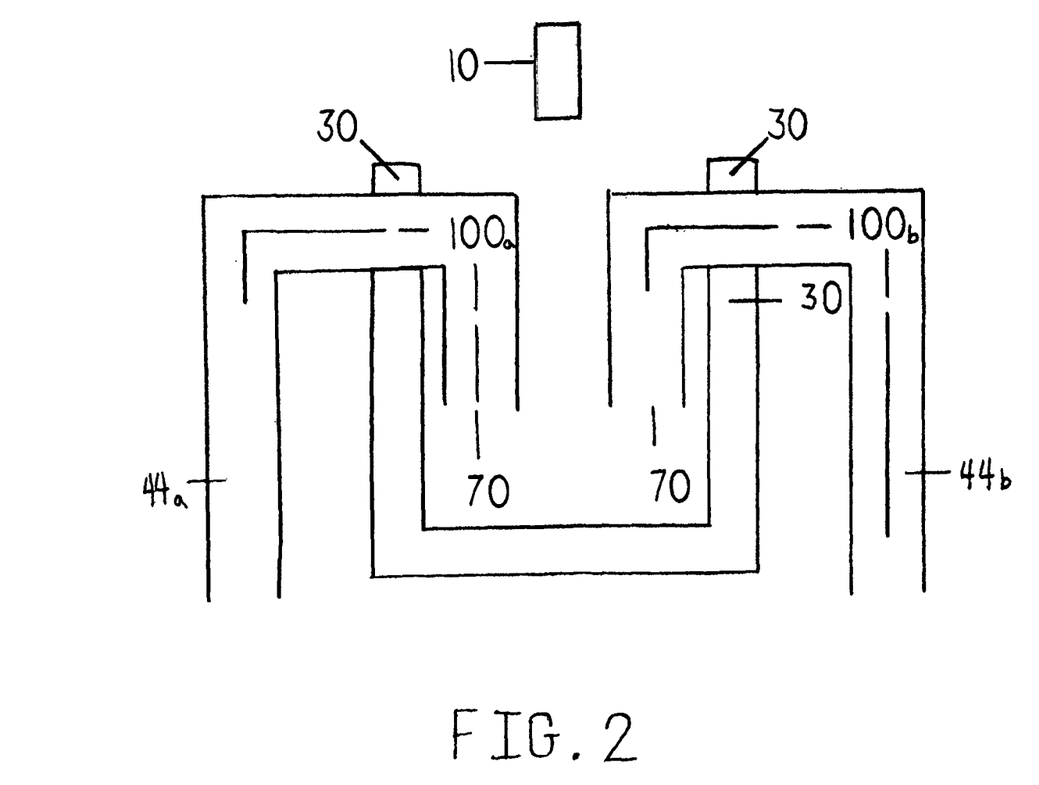
FIG. 2 shows a side view of example of method a double siphonic assembly 44

FIG. 2 shows a version of method including a siphon 44a and a second siphon 44b, method can have more than one siphon 44.

Method can have a siphon centerline 100, siphon centerline 100 can be a reference line depicting the path or route of siphon 44.

Siphon centerline 100a can depict path of siphon 44a.

Siphon centerline 100b can depict route of siphon 44b.

Figure 3:
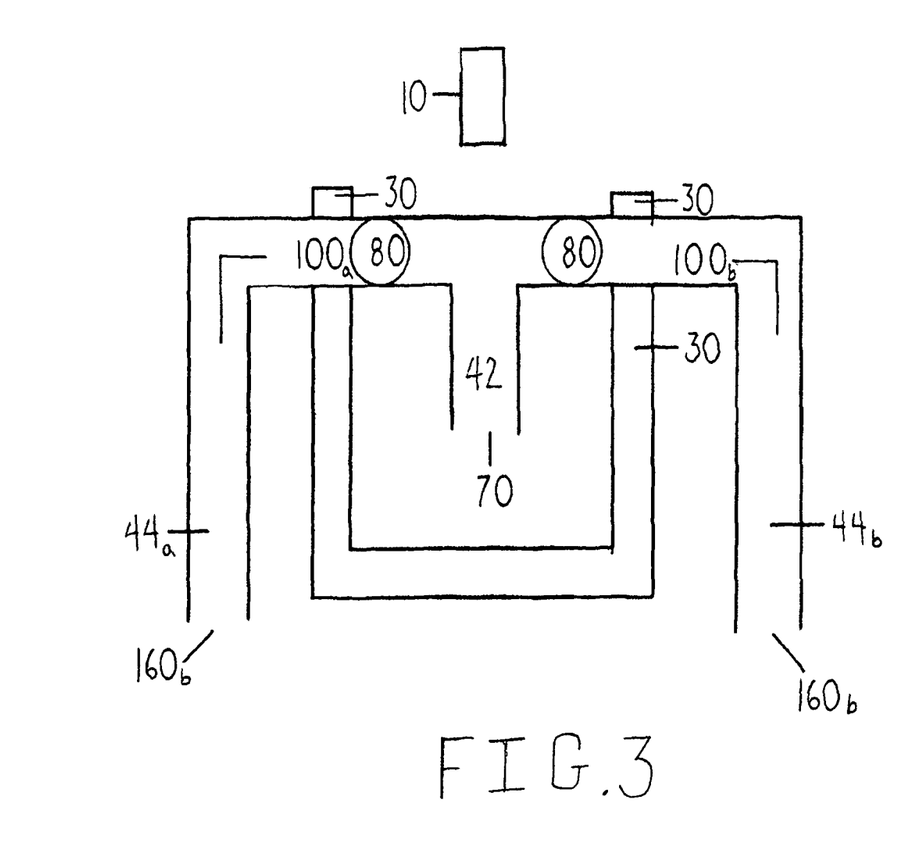
FIG. 3 shows a side view of example of method a double siphonic assembly 44 with a cooperative siphon supply 42

FIG. 3 can show a example of method.

A cooperative supply 42 can be any device capable of transferring a liquid, particularly in the form of a siphon.

Cooperative supply 42 can transfer a water supply 10 from a siphon inlet 70 towards a siphon outlet 160.

Cooperative supply 42 can transfer a water supply 10 from siphon inlet 70 to siphon 44a at a location near siphon apex 120 where then siphon 44a can transfer water supply 10 along siphon centerline 100a towards siphon outlet 160a.

Cooperative supply 42 can transfer a water supply 10 from siphon inlet 70

To siphon 44b which can be but not limited to being near siphon apex 120 where then siphon 44b can transfer water supply 10 along siphon centerline 100b towards siphon outlet 160b.

Cooperative supply 42 can contribute to method in any way useful.

A siphon check 80 can be a device which prevent water supply 10 from being transferred from a siphon 44a to a siphon 44b.

Siphon check 80 can be a check valve which prevent movement of a liquid in a given direction, can be any device to control movement of water supply 10.

Figure 4:
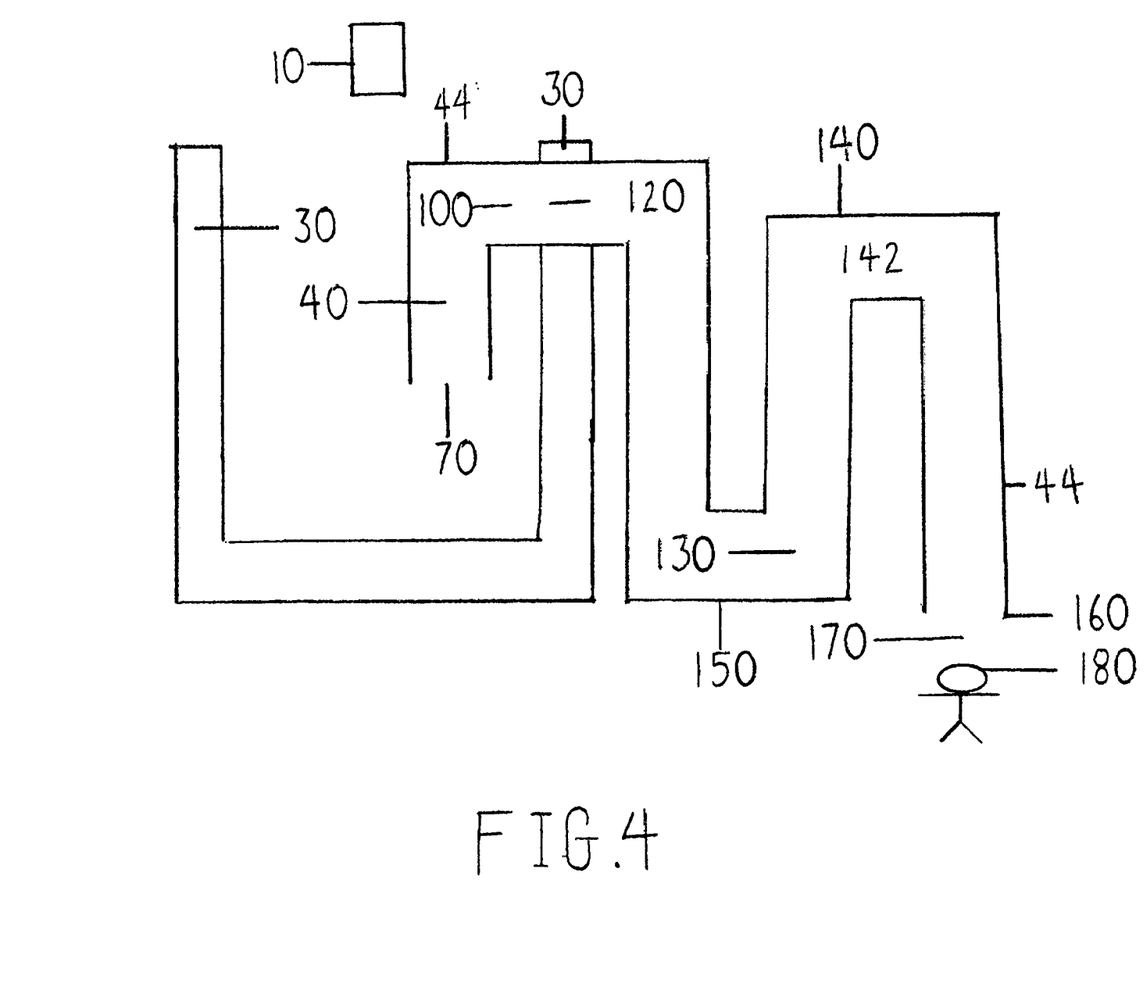
FIG. 4 shows a side view of an example of method a siphonic assembly 44 with a siphon Dip 130

FIG. 4 shows a example of method.

A siphon dip 130 can be a route of siphon centerline 100 that transfer a water supply 10 from a siphon apex 120 to a dip bottom 150 then to a dip top 140 at or near a dip apex 142 where water supply 10 can then be transferred towards a siphon outlet 160 and a person 180.

A siphon dip 130 can have a function of time delay, can have a volume that requires a amount of time to be filled by water supply 10.

Siphon apex 120 can be above dip apex 142 siphon apex 120 can be at same height as dip apex 142, siphon apex 120 can be below dip apex 142.

Dip apex 142, dip bottom 150, dip top 140, and siphon dip 130 can be any

Device to make method useful, can be any device which receive water supply 10 over a time before transferring toward person 180.

Can contribute to method in any way useful.

Figure 5:
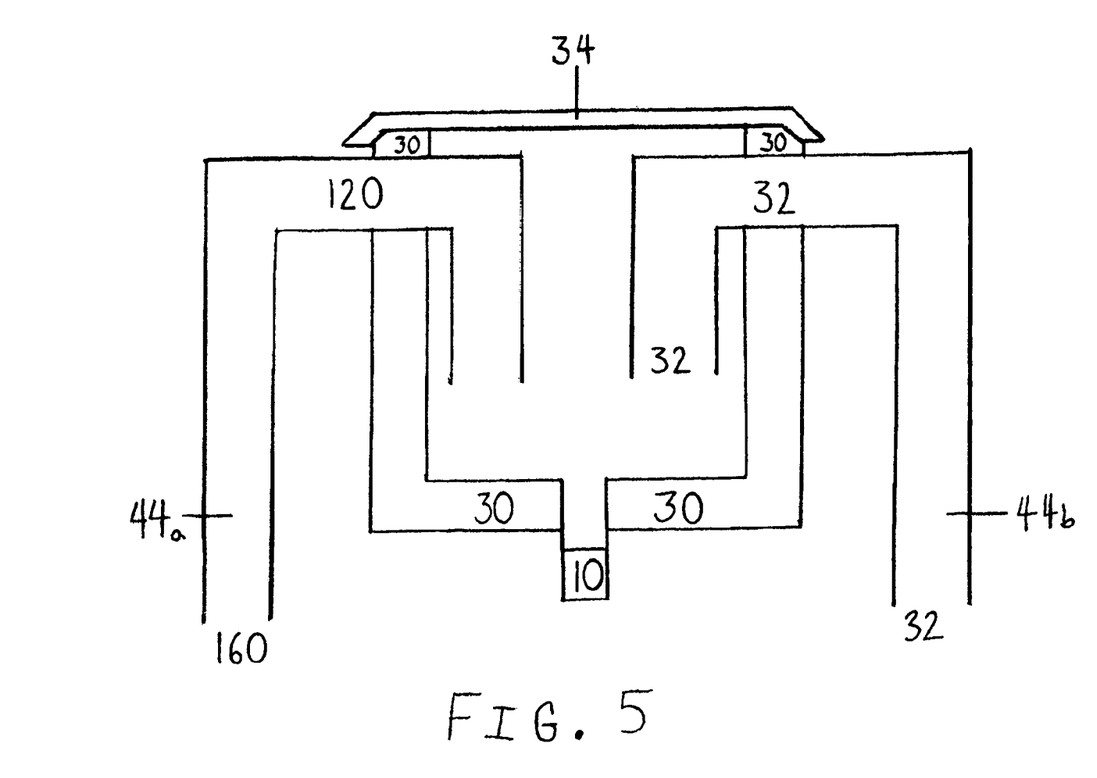
FIG. 5 shows a side view of example of method with a reservoir lid 34, a siphon supply 40 a siphon outlet 160 a reservoir vent 32 a medium 10

FIG. 5 shows an example of method.

A bucket lid 34 can be included in method, a bucket lid 34 can be removable, can be integral to bucket 30, can be modified in any way to make method useful.

Bucket lid 34 can be air tight, can be water tight.

A bucket vent 32 can be any device which allow air to enter bucket 30, siphon 44a, siphon 44b, siphon 44, any other parts of method.

Bucket vent 32 can allow air to enter bucket 30 and siphon 44a as water supply 10 be transferred from bucket 30 into siphon 44a, along thru siphon apex 120 towards siphon outlet 160.

Bucket vent 32 can allow air to fill volume of water supply 10 as water supply 10 transfer from bucket 30 toward siphon outlet 160.

water supply 10 can attach to bucket 30 upon bottom of bucket 30.

Components of method can reverse role from side siphon 44a to side siphon 44b, bucket vent 32 role can change side, siphon 44 of method.

Bucket vent 32 can contribute to method in any way useful.

Figure 6:
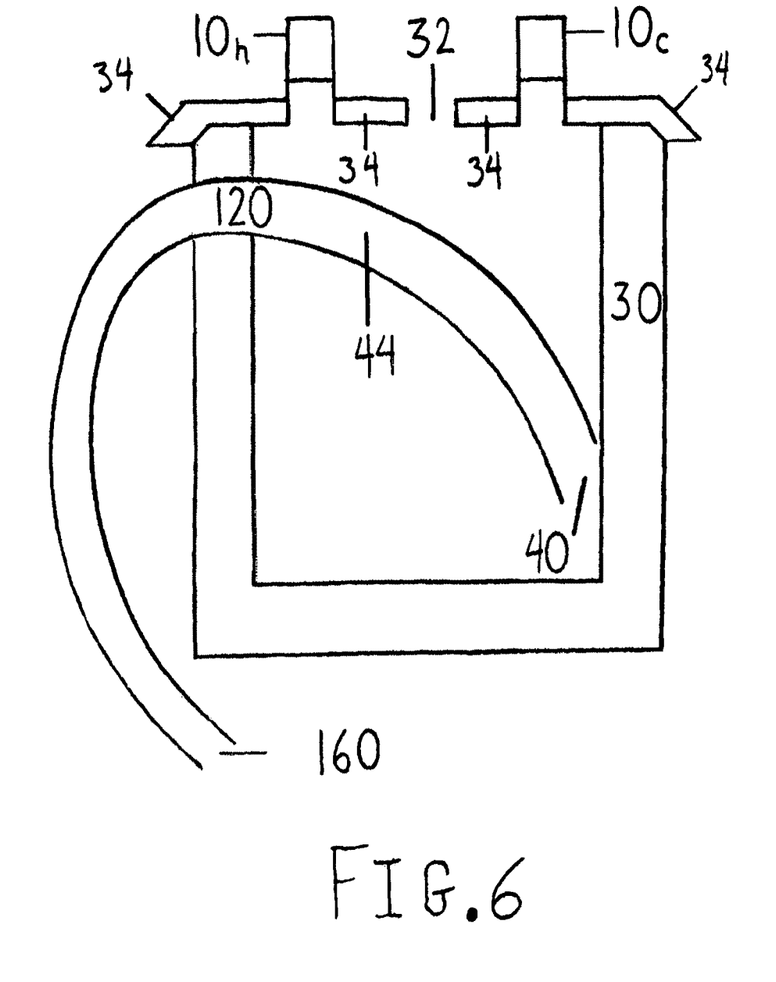
FIG. 6 shows a side view of example of method with a 48 flexible siphonic assembly, a reservoir vent 32 a medium 10h a medium 10c a reservoir lid 34

FIG. 6 shows example of method.

Siphon 44 can be a flexible device, can be a curved device, can be any device useful.

A bucket vent 32 can be attached upon the bucket lid 34.

A water supply 10h can supply hot water, a water supply 10c can supply cold water.

a water supply 10c and water supply 10h can be mixed before method before bucket 30, outside bucket 30, mixed water can be water supply 10 after mix.

Figure 8:
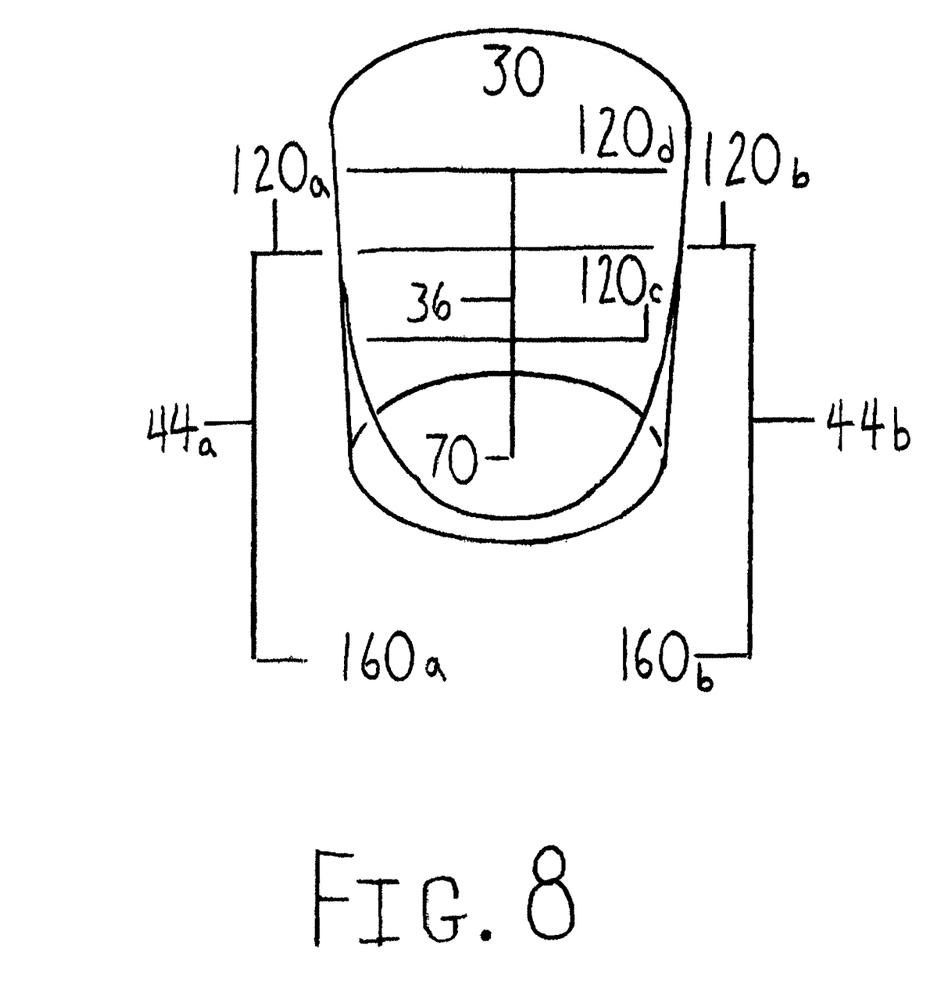
FIG. 8 shows an overview of method

FIG. 8 shows an example of method. A bucket assembly 36 can provide adjustable siphon apex 120 connections. Bucket assembly 36 can be an insert which fit with a common bucket, fit in a common bucket making common bucket a bucket 30. Can offer more than one siphon apex connection. Adjustable siphon apex connections can allow a user 180 to adjust volume of water transferred thru siphon 44. A user 180 can connect a siphon 44a to bucket assembly 36 at a connection providing a siphon apex 120a can connect a siphon 44b or section of siphon 44 to a connection providing a siphon apex 120b.

Connection can be thru bucket 30 side and made water tight, an adjustable siphon apex 120d connection and adjustable siphon apex 120c can be made available allowing a user 180 to remove siphon 44 and reattach at a different adjustable siphon apex 120.

Adjustable siphon apex 120 can be included in any version example of method.

Adjustable siphon apex 120 can be any device to make useful.

User 180 can provide their own common bucket and drill holes at points of connection allowing purchase of only bucket assembly 36.

Figure 7:
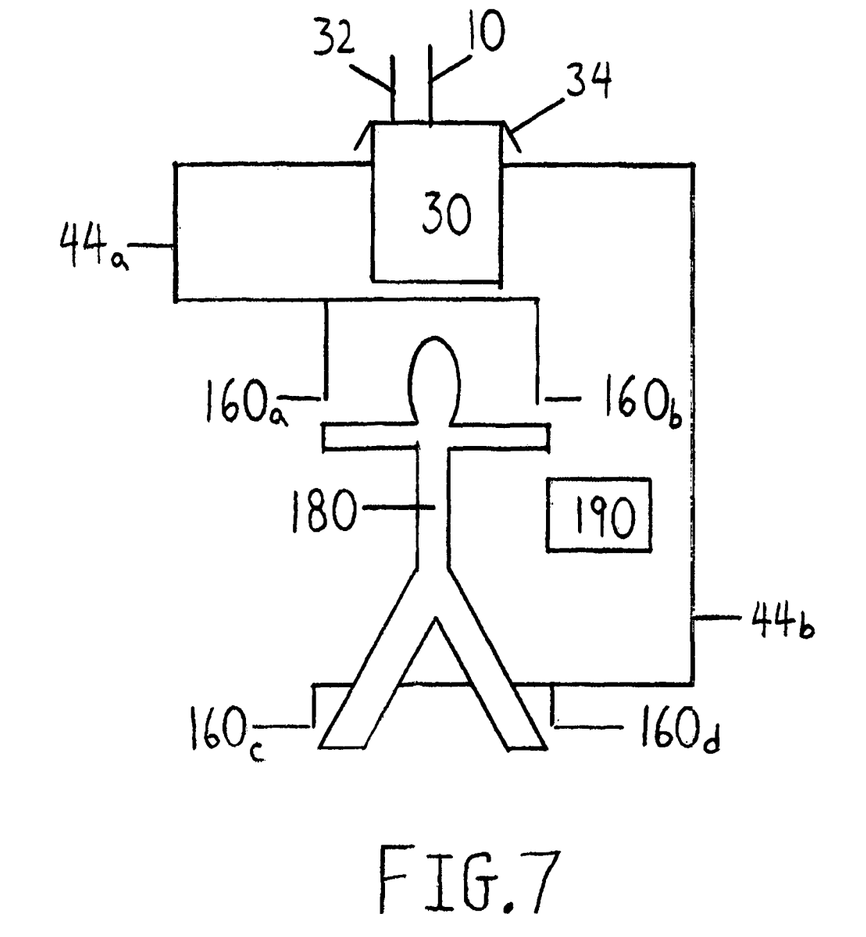
FIG. 7 shows a side view of an example of method a double siphon assembly each siphon assembly with multiple siphon outlet 160a 160b and 160c and 160d, a reservoir 30 a reservoir lid 34 a reservoir vent 32 a medium 10 a user 180a appurtenance 190

FIG. 7 shows a example of method.

A siphon 44a can have a siphon outlet 160a and a siphon outlet 160b.

A siphon 44b can have a siphon outlet 160c and siphon outlet 160d.

A siphon 44 can have multiple siphon outlet 160.

Figure 9:
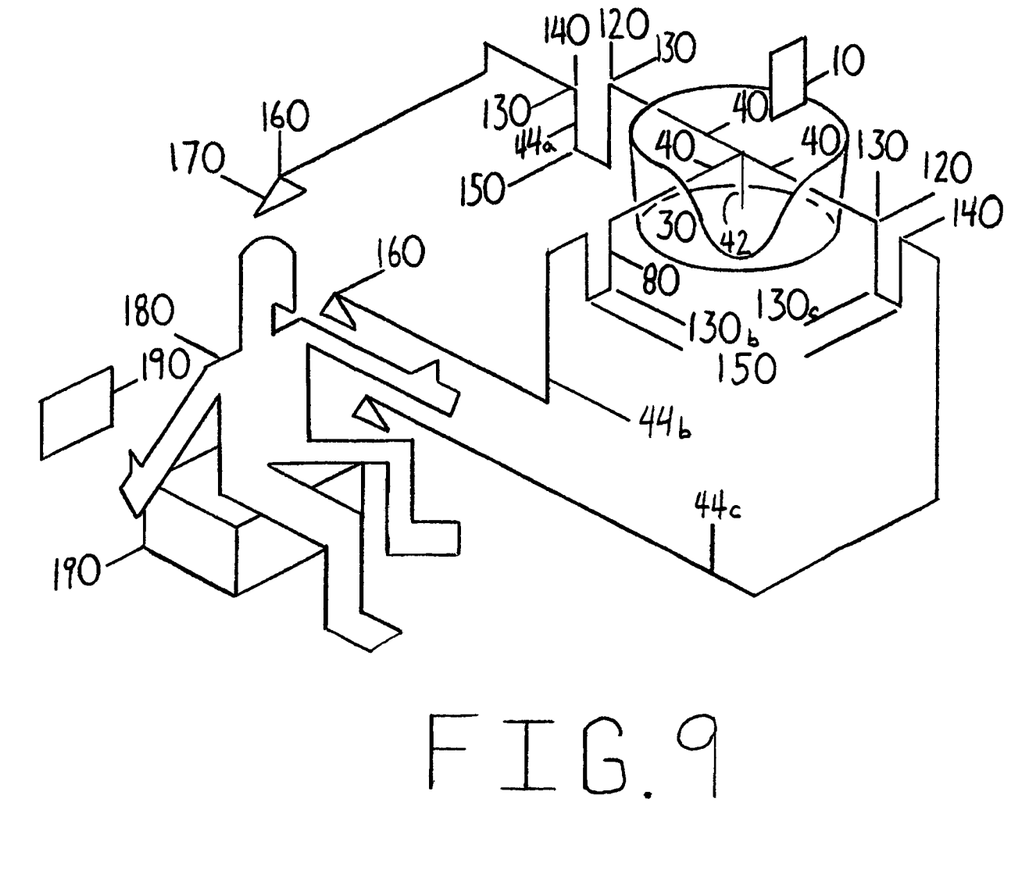
FIG. 9 shows an example of method a cutaway isometric view of a triple siphonic assembly each with a siphon dip a seated user 180 upon a seat appurtenance 190 using an appurtenance 190 and experiencing a benefit.

FIG. 9 shows a example of method.

Can include a appurtenance 190 to method.

Appurtenance 190 can be a seat, a handle, a bar, a device to display temperature of water supply 10, a device to display flow rate of water supply 10, a physical therapy device, a exercise device, a visual device light, a auditory sound device, a app on a phone or smart device or other technology, a social media, a valve, a control valve, any device which make a useful method, more useful.

Method can have more than one appurtenance 190.

A combination of siphon dip 130a, siphon dip 130b, and siphon dip 130c can transfer water supply 10 towards person 180 in a sequential pattern, general sequential pattern, water supply 10 can transfer thru a first Any given siphon 44, for example first siphon 44a, then second siphon 44b, then third siphon 44c, then repeat and siphon 44a can transfer again.

The water supply 10 can fill evenly the siphon 44 and therefore fill evenly the siphon dip 130 to produce sequential pattern sequential pattern can decrease chance of random pattern.

Appurtenance 190 can be a exercise, can be a yoga stance, can be a breathing technique, can be tai chi, can be a smoking cessation modality, can be a meditation.

Can be any activity which make method useful.

Figure 10:
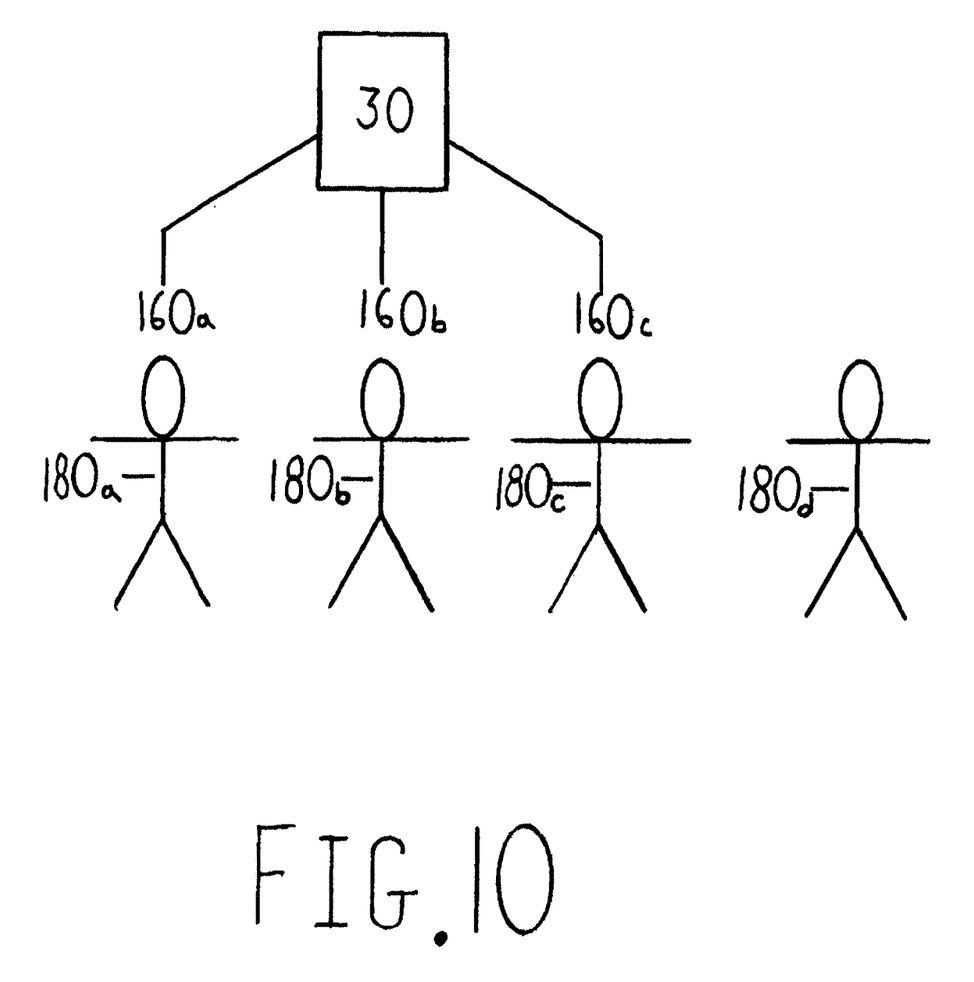
FIG. 10 shows an example of method a triple siphonic assembly leading to a person 180a, person 180b, and person 180c

FIG. 10 shows a example of method.

A person 180a, person 180b, a person 180c, a person 180d can play a game using method.

Any rules of game can be part of game.

A rules of game be persons 180 can use method in a non sequential a random pattern of water supply 10 transfer to siphon outlet 160, a random pattern.

Which ever persons 180 receive water supply 10 transfer at their location can then remove themselves after being watered and person 180d can choose to take spot of previously watered and removed which ever person 180 water supply 10 transfer or take another persons 180 spot and send them to spot of location where watered person 180 remover last water supply 10 transfer.

Persons 180 can be located a distance away from each other per social distancing guidelines.

Figure 11:
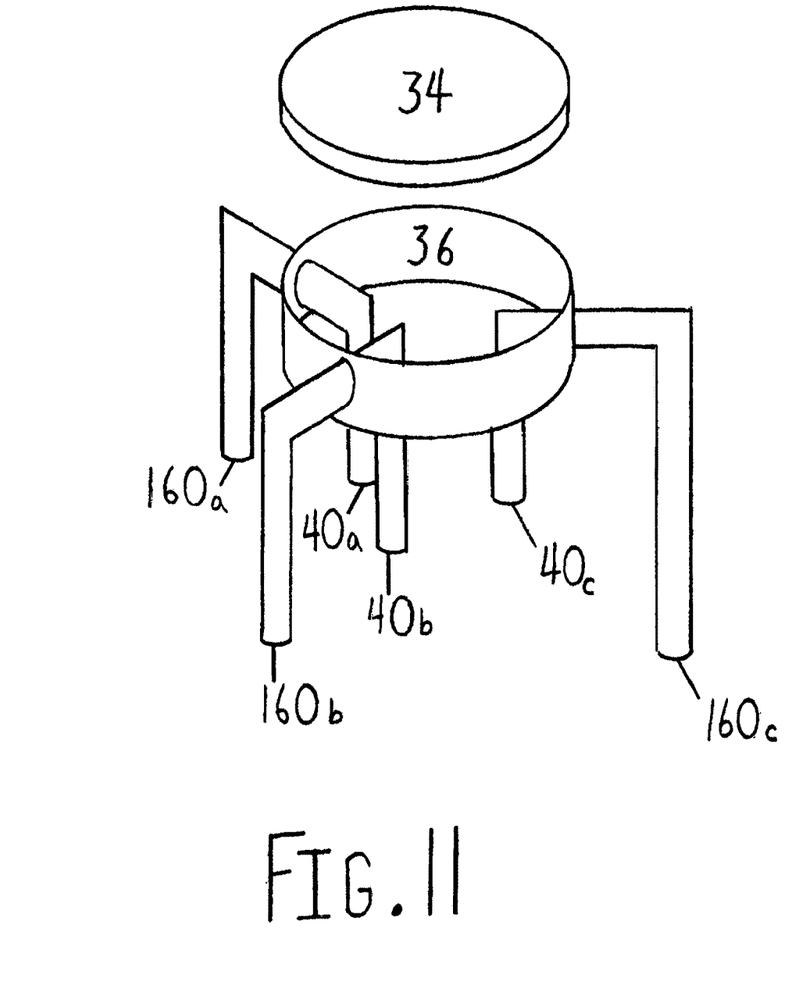
FIG. 11 shows a reservoir ring 36 with a triple siphonic assembly with a siphon inlet 40a, 40b, and 40c and a siphon outlet 160a, 160b, and 160c.

FIG. 11 shows a example of method. A bucket assembly 36 can be made to fit a standard bucket and bucket lid 34.

Bucket assembly 36 can be a profile to snap on to any standard bucket found at store turning a standard bucket into a bucket 30 of method.

Bucket lid 34 can snap on bucket assembly 36.

Snap on can be any means to attach including gasket, a zip tie, a tape, clips, bolts, screws, or any other way to attach that make useful.

Additionally water supply 10 can drain upon yard or lawn.

Method can be unattached to any building sewer, building drain.

method can drain on grass or any plants a person wants watered

Method can be used in any way found useful including but not limited to, a game, exposure to cold water to get physical mental benefits thereof.

Exposure to hot water can be used to get physical and mental benefits thereof; especially in colder times of fall, winter, spring, hot water exposure or warm water exposure may be enjoyable experience.

Person 10 can use a hot water source, and cold water source. and mixed water source, Water supply 10 can be adjusted with mixing valve or in bucket 30.

Temperature can be adjusted any way useful.

DESCRIPTION OF PREFERRED EMBODIMENT

Preferer embodiment of method can be to place a number of siphon outlet 160 around a number of person 180 and arrange a water supply 10 to fill a bucket 30 to a point near a siphon apex 120 with a water at a temperature which then can transfer location thru a siphon 44 towards person 180 and generate a useful benefit.

Person 180 can choose select a temperature of water supply 10, a flow rate of water supply 10, a location of a number of siphon outlets 160 supplied from a number of siphon 44 supplied from a bucket 30 with a source of water from water supply 10 then position themselves person 180 in conjunction with method to experience a exercise or Description of Additional Embodiments Additional embodiments can be construct a game around method.

Can be a game of chance featuring rotation of persons 180 exposure

Game can utilize the time between transfers of water thru siphon 44 the exposures of water to persons 180.

A rules of game can be and not be limited to; a number of players position themselves at locations where they will get water dumped on them if their siphon outlet 160 of location receive water from siphon 44, and when a person 180 get dumped on or get watered they get up from location, then a next person 180 who was next in line can either position themselves where previous watered person was or choose to bump another person 180 form their location to location of watered person and take their location.

And repeat.

While water supply is on.

Therefore including the benefits of cold water exposure into a pleasant experience.

To win game a person 180 can get watered or stay dry depending on rules, possibly weather.

A persons 180 of game can focus their "invisible energy" at siphon, at bucket, at method components, at ground, where ever as novelty of game.

Description of Additional Embodiments

Additional embodiments can be to build a insert comprising components of method and which can fit in conjunction with a bucket 30.

Providing a number of siphon outlet 160 a number of siphon 44, and any other components of method.

Insert bucket assembly 36 can not require modifications, holes to be added to bucket 30, can require modifications holes.

Which can be a bucket assembly 36 can contain components of method allowing a person 180 to use bucket assembly 36 with a bucket 30 to enact method.

This can provide for a easy to store, easy to clean, easy to replace functionality to method.

Bucket assembly 36 can include a volume of bucket displacing device.

Bucket lid 34 can also be inclusive to insert and or bucket assembly 36.

Volume of bucket can replace a volume of water in bucket 30 with non-water.

Volume of bucket can allow for adjustment of volume of transfer.

Bucket assembly 36 can be collapsible or shrinkable or compressible, can be made to change volume, can make easy to ship or store.

Can be made out of flexible material, can have a bellows quality or design allowing volume change.

Bucket assembly 36 can provide adjustable siphon apex 120 connections providing option to change volume of water to be transferred by siphon 44.

Person 180 can chill holes in a bucket 30 to access adjustable siphon apex 120 connections.

Description of Additional Embodiments

As the degree of cold exposure can relate to degree of usefulness of method a extreme exposure embodiment can include a source of ice, which could be positioned within bucket 30, within water transferred thru method.

Physical effects on body of user 180 can help physical effects daily stress, fatigue, other conditions have.

Person 180 can use method to achieve physical goals including and not limited to; preventing exposure to a virus, which can be covid 19, living with a virus, living with a chronic disease such as MS diabetes PTSD anxiety Crohn's disease eczema dementia nicotine cessation substance abuse alcoholism or any other.

Method may offer physical changes in a person 180 make up, their blood chemistry lymphatic system, vascular system, connective tissue or reduce pressure thereof.

Weight loss as a calorie is defined as a measure of heat exposure to cold is to generate more heat.

Description of Additional Embodiments

Method can provide mental, psychological, benefits to a person 180.

Benefit may be to enjoy time with friends and family in constructive activity, excitement of watching them get cold water dumped on their heads and vice versa.

Benefit of mental clarity, focus, composure and strength.

Cold water exposure can be a very real experience a connected experience grounded, which can be additional usefulness as person may be bare foot in use of method.

During exposure user 180 can let go forget any stress, anxiety, guilt, fear, or other derogatory mental backdrops a user 180 may carry.

It can help with grief of losing a loved one, help with mentality related to nicotine cessation, substance abuse, alcoholism.

It can be a coping mechanism for those who have experienced traumatic events causing PTSD or been a victim of any kind of abuse including physical, sexual, and mental.

A time of relaxation for person 180 with ADHD, ADD, mood disorder, depression, and any others.

This benefit can provide great memories experiences between a person 180 and spouse, together with love in their life.

fully taking in the moment together, experiencing method together.

A high involvement mental battery recharge.

Additionally any device or method can be used to produce usefulness of method.

Any method or device described can be removed or combined to provide usefulness, of method.

Advantages

From description any advantages of method can be evident.

Operation

Person 180 can arrange components, parts, of method in any way that make useful.

Conclusion, Ramifications, and Scope

Accordingly the reader will see method provides a variety of ways for a person to experience a exposure with a water at a temperature with a device which can be include a siphon and a bucket and experience a benefit, usefulness, goal, thereof.

Therapeutic can mean physical,

Therapeutic can mean psychological.

Therapeutic can mean exercise.

Adjustable siphon apex 120 can have a hose connection.

Adjustable siphon apex 120 can be a hose connection which can connect to bucket assembly 36.

Bucket assembly 36 which connect to adjustable siphon apex 120 can be a hose, a hose connection adjustable siphon apex 120 can be a hose, a hose connection.

Any spelling errors, grammatical errors can change their form meaning to give most clarity.

Water supply 10 can be the liquid used in method, can be the valve controlling flow of liquid, can be any device useful.

Method can be useful to a person lawn or plants.

Description of Method

Person 180 can use appurtenance 190 a partition, a portable wall Partition portable wall can add element of privacy and protection from elements, wind snow rain etc.

Appurtenance 190 a partition can offer sun protection, any other useful benefit.

Any shape profile, can be built integral into bucket 30, can be integral of a bucket 30 which is any device capable able to hold water, can be any device which contribute to method in any way useful.

A siphon inlet 70 can be a location that water supply 10 can enter siphon 44 from bucket 30.

Siphon inlet 70 can be at a bottom of bucket 30, can be below bottom of bucket 30.

Siphon inlet 70 can contribute to method in any way useful.

A siphon apex 120 can be a location that water supply 10 can be filled toward siphon apex 120 can be location inside siphon 44.

Water supply 10 can fill past siphon apex 120.

Siphon Apex 120 can be location inside siphon 44.

Siphon apex 120 can be adjusted up and down.

Bucket 30 can be adjusted up and down, tilted tipped, to adjust siphon apex 120, siphon apexes 120 can have a location within bucket 30.

Siphon apex can be a horizontal plane used for reference in connection to method and components of method.

Siphon apex 120 can be the high point a water supply 10 approach in siphon 44 and bucket 30 and rest of method.

Siphon apex 120 can contribute to method in any way useful.

A siphon outlet 160 can be a location water supply 10 can exit siphon 44.

Siphon outlet 160 can be below siphon inlet 70.

Siphon outlet 160 can be located in conjunction with a person 180.

Siphon outlet 160 location can contribute to method in any way

Siphon outlet 160 can be located in multiple locations as wanted

Description of Method

FIG. 1 shows a basic version of method including any water supply 10 which can be sourced from stored rain water, city water pipes, a well, or any other source of water.

Water supply can have a contributing feature of temperature, or quality of temperature.

water supply 10 can be cold water cool water warm water or hot water, any temperature that make method useful.

A bucket 30 can be a bucket or any device able to hold water, to contain water, to process water in any way useful.

Bucket 30 can be modified in any way to make method useful.

Modifications can be to have holes placed in the side walls or bottom to allow components of method to make method useful.

Bucket 30 can be modified in way to make water tight connections with components of method, can be modified to allow to drain with components of method.

A siphon 44 can be any device capable of transferring a liquid particularly in the form of a siphon, having the ability to move a liquid from a height to a lower height but first to a higher height.

Siphon 44 can be a pipe, a tube, a device of

Description Preferred Embodiment

Invention can mean method.

Figure 12:
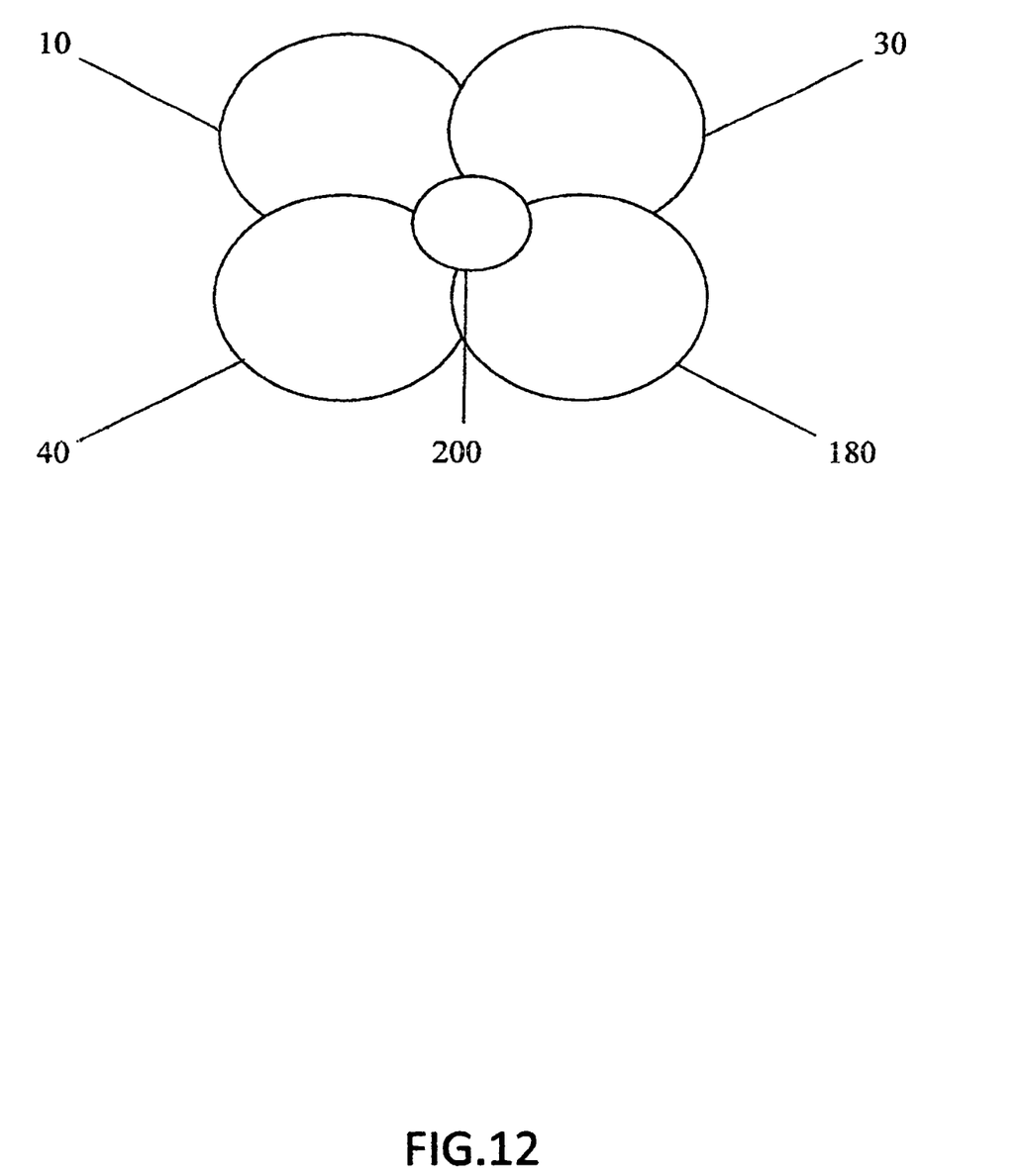
FIG. 12 shows an example of Invention including a Water Supply 10, a Bucket 30, a siphon 40, and a User 180

A preferred embodiment of present application can be, and not limited to being, illustrated in FIG. 12 showing a Water Supply 10, a Bucket 30, a siphon 40, a User 180, a Usefulness 200. A water supply 10 can have means to provide water into bucket 30 this filling of bucket 30 can require a time. A siphon 40 can be attached to bucket 30. When water fill bucket 30 to a point, a volume, a height relating to siphon 40, siphon 40 can direct water thru siphon 40 moving water from bucket 30 out of bucket 30 at a rate greater than water supply 10 provide water into bucket 30. Water can be directed from siphon 40 towards a location, user 180 can position in relation to location to get usefullness 200 of invention. Invention can provide a intermittent, non-continuous water directed toward a location allowing a user 180 to receive any usefulness of invention.

Water Supply 10 can provide a means for water delivery. Water Supply can be any device capable of delivery of a water to invention.

Water Supply 10 can be an indirect connection, can be a air break or air gap providing a delivery of water to invention with a proximity to invention. Indirect connection can b positioned at a proximity to invention that allow water delivery to invention. Can be any device with means for water delivery to invention.

Water Supply 10 can be a direct connection, can be a hose connection, can be a pipe connection, can be a threaded connection, can be a soldered connection, can be a flared connection, can be a quick connect connection, can be a welded connection. Can be any device with means for water delivery to invention.

Water Supply 10 can be a hand drawn connection. Hand drawn connection can be a manual delivery of water to invention. Manual drawn connection can be a water delivery from a location then brought to invention and deposited with in invention.

Water can originate from a cold water source, water can be from a hot water source, water can be from a thermostatically mixed source such as a thermostatic mixing valve or other valve with construction to mix cold and hot water.

Water can originate from a rain water or rain collection device. Water can originate from a lake. Water can originate from a river. Water can originate from any water source making invention useful.

Water can originate from any water source found useful.

Invention can have a bucket 30.

Bucket 30 can have an attachment to water supply 10.

Bucket 30 can have an attachment to siphon 40.

Bucket 30 can be any device able to hold water and make invention useful.

Bucket 30 can be a purpose built device specifically designed for invention.

Bucket 30 can have an integral construction including siphon 40

Bucket 30 can have an integral construction including water supply 10

Bucket 30 can have an integral construction including a water supply 10 connection.

Bucket 30 can be constructed with any material found useful. Can be constructed with any shape found useful. Can be constructed with any size found useful.

Bucket 30 can be a common article including and not limited to a common bucket, a bottle.

Bucket 30 a common article can have required modifications made to it to make invention useful.

Bucket 30 a common article can have modifications made to it to provide connection to water supply 10

Bucket 30 a common article can have modifications made to it to provide connection to siphon 40.

Bucket 30 can be any device with means to hold water, make invention useful

Bucket 30 can have a vent. Vent can allow air to exit bucket 30 as water fill into bucket 30.

Bucket 30 can have a vent. Vent can allow air to exit bucket 30 as water fill a limited section of bucket 30.

Bucket 30 can have an adjustable vent. Vent can allow air to exit bucket 30 as water fill a limited section of bucket 30.

Invention can have a siphon 40.

Siphon 40 can be any device with a construction able to transfer a liquid using gravity.

Siphon 40 can be any device with a construction able to transfer a liquid using a venturi.

Siphon 40 can be a purpose built device specifically designed to make invention useful.

Siphon 40 can have a connection to bucket 30.

Siphon 40 can have a inlet located in conjunction with bucket 30.

Siphon 40 can have a outlet located in conjunction to inlet.

Siphon 40 inlet can be connected so as to allow liquid flow from bucket 30 allowing for water to move out of bucket 30 from inlet towards outlet.

Siphon 40 can extend from siphon inlet in a generally upwards construction to a siphon apex then extend downwards to a siphon outlet.

Siphon 40 siphon apex can be a location of which when water fill to this point water will move towards siphon outlet.

Siphon 40 can have a siphon inlet at or near bucket 30 siphon 40 can then extend upwards to a siphon apex then extend down wards to a siphon outlet providing for as water fill up bucket 30 and simultaneously water fill up siphon 40 at the water fill height of siphon apex water can then move from bucket 30 thru siphon 40. Water can fill bucket 30 and siphon 40, when water reach a point which can be siphon apex siphon 40 will transfer water from bucket 30 thru siphon inlet up to siphon apex then down to siphon outlet.

When water from water supply 10 fill up bucket 30 to a height, water from Water Supply 10 can be directed from bucket 30 thru siphon inlet then thru siphon apex then thru siphon outlet towards a location.

Siphon 40 can be constructed with a high point. High point can be positioned between siphon 40 inlet and siphon 40 outlet. Siphon 40 high point can be positioned between siphon inlet and siphon apex. Siphon 40 high point can be positioned between siphon apex and siphon outlet.

Siphon 40 can be constructed with a low point. Low point can be positioned between siphon inlet and siphon outlet. Siphon 40 low point can be positioned between siphon inlet and siphon apex. Siphon low point can be positioned between siphon apex and siphon outlet.

Siphon high point siphon low point can produce a air column as invention operate, air column with in siphon 40 can provide for a irregular or unscheduled operation. Can provide means to produce irregular or unscheduled operation of siphon 40.

Invention can have a user 180. User 180 can be a person. User can be any person who can benefit from invention.

User 180 can locate position in relation to invention to make useful.

User 180 can locate in a position in relation to siphon outlet and therefore in a position of water from water supply 10 as it moves from bucket 30 thru siphon 40 out siphon outlet.

User 180 can locate in position to invention to contact a body segment with water from siphon outlet.

User 180 can locate in a position to invention to contact a body segment with water from siphon outlet including and not limited to, arms, legs head, neck shoulders, chest, stomach, back, lower back, glutes, hands, feet.

User 180 can locate in a position to invention to perform exercise movements in conjunction with invention.

User 180 can locate in a position to invention to perform yoga asanas in conjunction with invention.

User 180 can locate in position to invention to accomplish any usefulness of invention.

User 180 can locate in position to invention to watch other user use invention.

User 180 can locate in position to invention with a partition portable wall constructed with the qualities including and not limited to, provide a element of privacy, provide protection from elements sun rain, snow wind.

Usefulness can be a physical nature, including and not limited to, change in blood pressure, change in body fat percentage, pain relief, reduction of pressure on joints, muscle tone, calorie burning, strength training, heart disease, cancer treatment prevention, allergy mitigation, multiple sclerosis mitigation, covid prevention treatment, any other physical usefulness.

Usefulness can be a psychological nature including and not limited to, anxiety treatment, mood disorder, stress, post traumatic stress disorder, physical or mental abuse, any other psychological usefulness.

Usefulness 200 can be a smoking cessation program, including and not limited to placing invention outdoors at location of nicotine use.

Usefulness 200 can be a vaccine side effect mitigation that a user 180 can use invention to reduce side effects of vaccine side effects before and or after vaccine.

Usefulness 200 can be a game participation, a plurality of user 180 can get together and follow a game including invention.

Usefulness of game participation can include a plurality of any of following; siphon 40, bucket 30, user 180 water supply 10 arranged in a game format where user 180 can benefit usefulness of invention and spend time with friends and family. A user can watch friends family get cold water dumped on them.

Usefulness of game can be any rules of game including and not limited to, three siphon 40 be arranged upon a bucket 30, three user 180 position in location of siphon 40 outlets, whichever of user 180 the siphon 40 dumps water on them can get a score and a new user 180 can replace dumped on user 180, or take another user 180 location forcing the displaced user into remaining location.

We claim:
1. A siphon apparatus comprising:
a bucket;
a water supply for filling said bucket with water;
at least one siphon which during operation causes water to be removed from said bucket;
said at least one siphon including a siphon inlet, a siphon apex, at least one dip, and a siphon outlet;
said siphon apex located downstream of said siphon inlet and upstream of said siphon outlet;
said at least one dip located between said siphon apex and said siphon outlet and further including a dip bottom, and a dip top having a dip apex and said dip apex being located downstream of the dip bottom;
wherein as said water supply fills said bucket with water, the at least one dip causes an air column to form within said siphon which causes an irregular or unscheduled operation of said siphon.

* * * * *